US00PP21765P3

(12) United States Plant Patent
Pounders, Jr.

(10) Patent No.: US PP21,765 P3
(45) Date of Patent: Mar. 8, 2011

(54) ***HIBISCUS* PLANT NAMED 'SAHARA SUNSET'**

(50) Latin Name: *Hibiscus acetosella*
Varietal Denomination: Sahara Sunset

(75) Inventor: Cecil T. Pounders, Jr., Poplarville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/454,676

(22) Filed: May 21, 2009

(65) Prior Publication Data

US 2010/0299794 P1 Nov. 25, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner*—Susan B McCormick Ewoldt
(74) *Attorney, Agent, or Firm*—John D. Fado; Evelyn M. Rabin

(57) ABSTRACT

A new and distinct cultivar of *Hibiscus* plant named 'Sahara Sunset', characterized by its spreading upright growth habit and unique multicolored maple leaf-shaped ornamental foliage saturated with two dominant color regions.

2 Drawing Sheets

Botanical designation: *Hibiscus acetosella.*
Cultiver denomination: 'Sahara Sunset'.

BACKGROUND OF THE INVENTION

The present invention relates to a new and distinct cultivar of *Hibiscus,* botanically known as *Hibiscus acetosella,* and hereinafter referred to by the name 'Sahara Sunset'.

The new *Hibiscus* was originated in Poplarville, Miss. and is a product of a mutation induction program. The parent of the present new cultivar is an unknown *Hibiscus acetosella* Wels. Ex Hiern seedling. The present new cultivar, selected as HAC06-11, is a seedling selection from a group of seedlings produced from seed of open pollinated purple leaf *Hibiscus acetosella* Welw. Ex Hiern. which were exposed to gamma-ray radiation from a Colbalt 60 source at the Agricultural Research Service, U.S. Department of Agriculture in Tifton, Ga.

'Sahara Sunset', identified as HAC06-11, was selected in 2006 and subsequently propagated asexually by vegetative cuttings in a controlled environment in Poplarville, Miss. multiple times since 2006. Resulting plants were evaluated at nurseries in California, Florida, Georgia, Minnesota, Mississippi, New Hampshire, and Texas. The unique features of 'Sahara Sunset' have reproduced true to type in successive generations; no aberrant types have appeared. 'Sahara Sunset' is the first stable variegated form of the purple leaf form of the *H. acetosella* species released to date.

SUMMARY OF THE INVENTION

The cultivar 'Sahara Sunset' has not been observed under all possible environmental conditions. The phenotype may vary somewhat with changes in environment and cultural practices such as temperature and/or light intensity without, however, any variance in genotype.

The following traits have been repeatedly observed and are determined to be the unique characteristics of 'Sahara Sunset'. These characteristics in combination distinguish 'Sahara Sunset' as a new and distinct cultivar of *Hibiscus acetosella:*

(1) Spreading upright growth habit.
(2) Unique multicolored maple-like ornamental foliage with two dominant color regions.

Plants of the new *Hibiscus* can be compared to plants of the parent, *Hibiscus acetosella* Welw. Ex Heirn. Plants of 'Sahara Sunset' differ primarily from the parent in leaf color as plants of the cultivar 'Sahara Sunset' have unique foliage saturated with two dominant color regions: burgundy gray with an outer band of pink. 'Sahara Sunset' has small insignificant purple flowers. Plants of the parent have deep red leaves and stems and dark maroon 2" flowers.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph at the top of FIG. 1 is a close up view of typical leaves of a 'Sahara Sunset' *Hibiscus* plant grown as an annual shrub.

The photograph at the bottom of FIG. 1 comprises a side perspective view of a typical plant of 'Sahara Sunset' *Hibiscus* grown as an annual shrub.

The photograph at the top of FIG. 2 comprises a side perspective view of a single typical plant of a 'Sahara Sunset' *Hibiscus* grown in a container.

The photograph at the bottom of FIG. 2 is a close up view of typical leaves of a 'Sahara Sunset' *Hibiscus* plant showing the unique foliage saturated with two dominant color regions: burgundy gray with an outer band of pink.

DETAILED DESCRIPTION OF THE NEW VARIETY

In the following description, color references are made to The Royal Horticultural Society (R.H.S.) Color Chart, 2001 Edition, except where general terms of ordinary dictionary significance are used. Plants used for the photographs and description were grown in Poplarville, Miss. during the late summer and under full sun field conditions which closely approximate commercial production conditions. During the production of the plants, day temperatures ranged from 28 to 36° C. and night temperatures ranged from 4 to 24° C. Plants had grown for about three months under optimum conditions from rooted cuttings when the description, photographs, and color values were determined.

Botanical classification: *Hibiscus acetosella* Welw. Ex Hiern.

Parentage: Gamma-ray (Colbalt 60 source) radiation-induced mutation of *Hibiscus acetosella* Welw. Ex Hiern.

Propagation:

*Type.*—By freshly hardened soft-wood cuttings.

*Time to initiate roots.*—About three weeks at 27° C.

*Time to produce a rooted young plant.*—About six weeks at 27° C.

*Root description.*—Fibrous; white in color.

*Rooting habit.*—Freely branching; moderately dense.

Plant description:

*Plant form and growth habit.*—Moderately vigorous growth habit. Spreading upright when grown as an annual shrub.

*Branching habit.*—Fruticose.

*Plant height.*—1-2 meters.

*Plant diameter.*—0.5-1 meter.

Lateral branch description:

*Length.*—0.5-1.0 meter.

*Diameter.*—1-2 cm.

*Internode length.*—3-6 cm.

*Texture.*—Smooth.

*Color.*—Red Purple 59C.

Foliage description:

*Arrangement.*—Alternate.

*Length.*—4-6 cm.

*Width.*—5-7 cm.

*Shape.*—Maple leaf shape; three to five lobes with pronounced sinuses.

*Apex.*—Acuminate.

*Base.*—Truncate.

*Margin.*—Irregularly dentate.

*Texture.*—Smooth, glabrous.

*Venation pattern.*—Pinnipalmate.

*Color.*—Upper surface with outer band (1-10 mm) — pink (Red Group RHS 54B fading to Red Purple 62D); Majority of leaf — burgundy (Red Purple RHS 59A fading to Grayed Green 188C). Lower surface same pattern but faded; outer band pink (Red Group RHS 54C); majority of the leaf burgundy (Red Purple RHS 59C).

Petiole:

*Length.*—3.5-7 cm.

*Diameter.*—1-3 mm.

*Texture.*—Upper and lower surface: Glaborous.

*Color.*—Greyed Orange 177B with overlay of Greyed Purple 185B.

Flowers:

*Flower type.*—Small with limited ornamental value.

*Season.*—November through April.

*Bloom life.*—One Day.

*Fragrance.*—None.

*Arrangement.*—Clustered 3-7 in some terminal leaf axils.

*Individual flower.*—4-8 cm.

*Symmetry.*—Radial.

*Color.*—Purple (Red Purple 58C) with dark veining in petals (Red Purple 58A) and basal eye (Greyed-Purple 187B).

*Petals.*—5, spatutate, length 2-3 cm, apex rounded, base truncate, margin entire.

*Pistils.*—1, 5 parted.

*Stamens.*—20-30.

Fruit/seed: None observed.

Disease/pest resistance: Plants of the new *Hibiscus* are tolerant of common insects and diseases.

Temperature tolerance: The new *Hibiscus* 'Sahara Sunset' is a tropical shrub and has been observed to be hardy to USDA Cold Hardiness Zone 10. In colder zones, where the plant would winter kill, the cultivar is well adapted for use as a summer annual adapted to summer heat and moisture stress. The cultivar is adapted to hotter dryer cultural conditions than many traditional bedding plants.

We claim:

1. A new and distinct *Hibiscus* plant named 'Sahara Sunset' as illustrated and described.

* * * * *

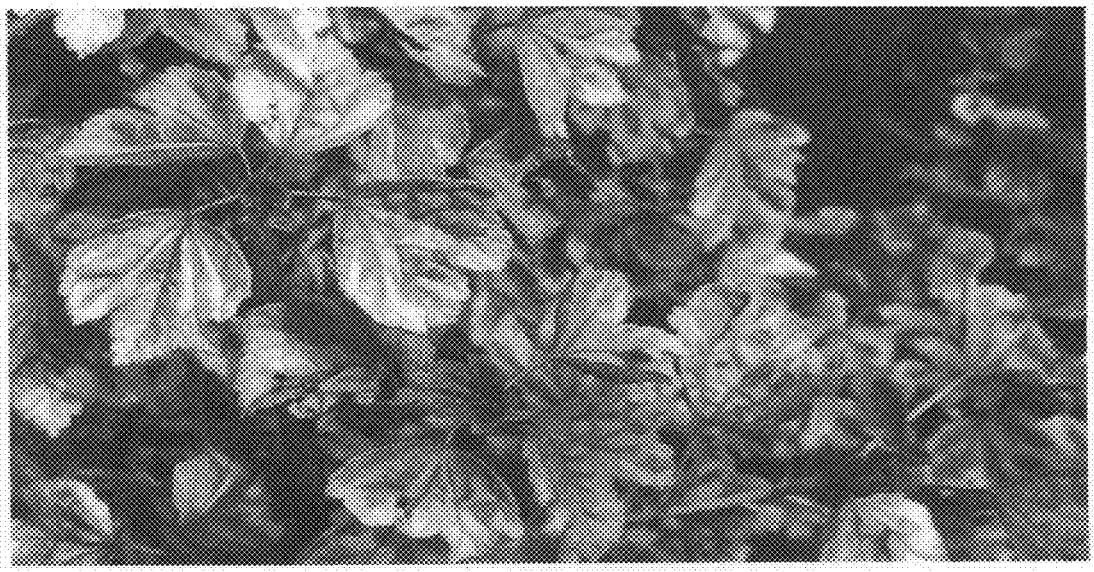
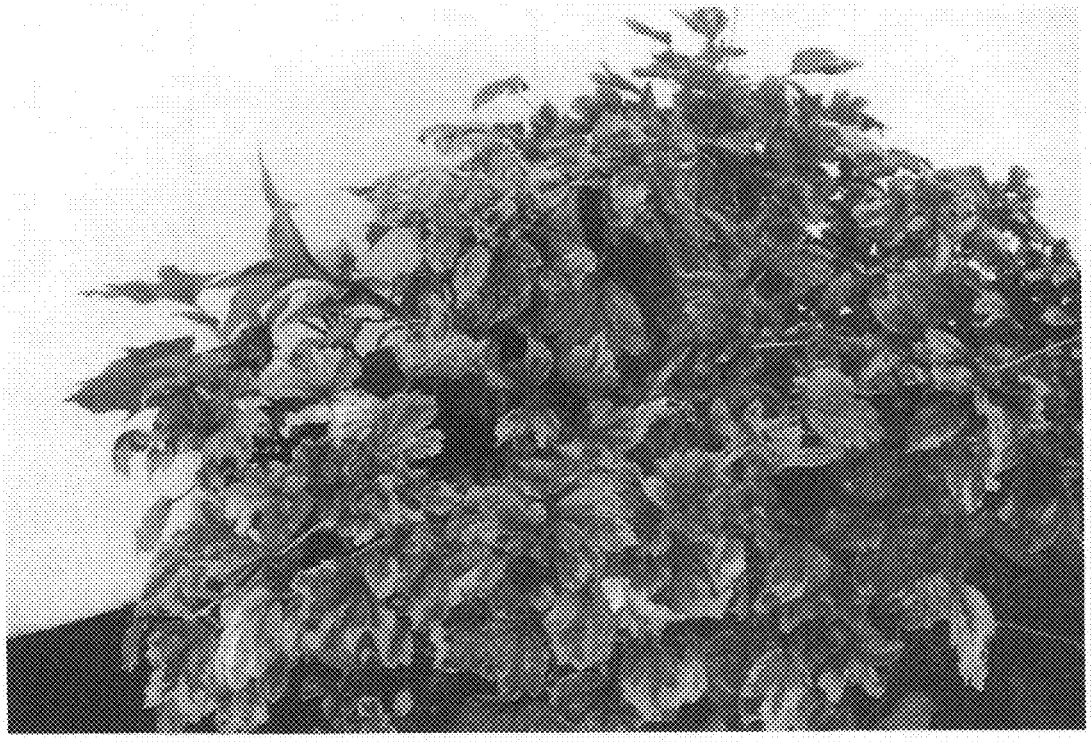
Sheet 1

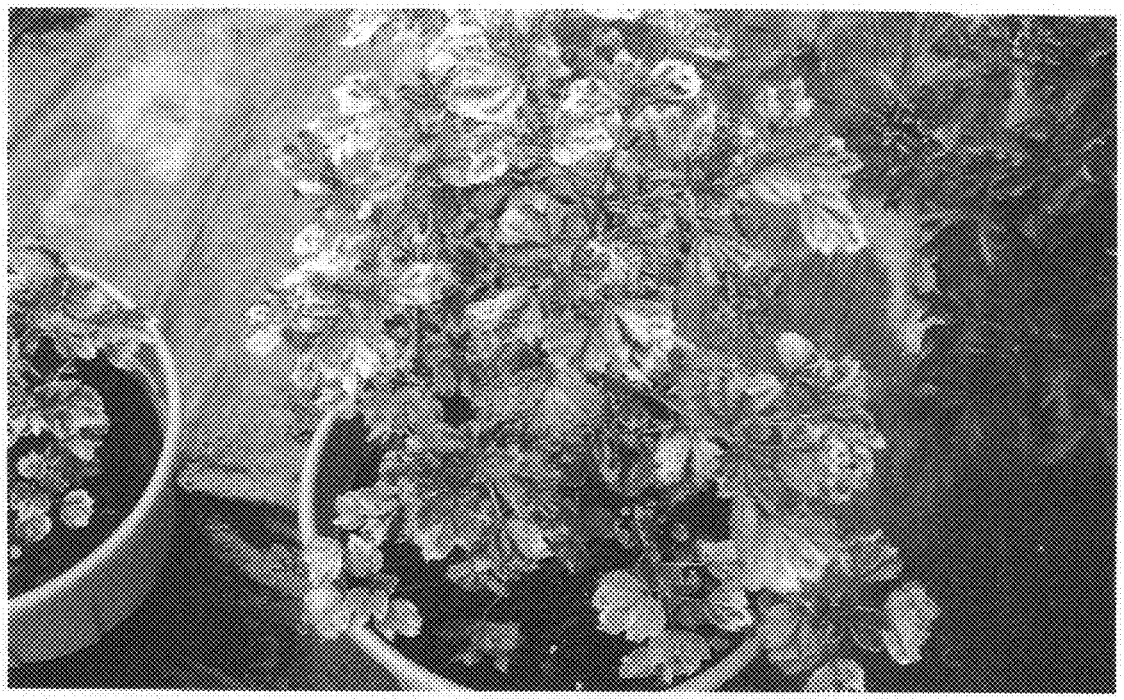
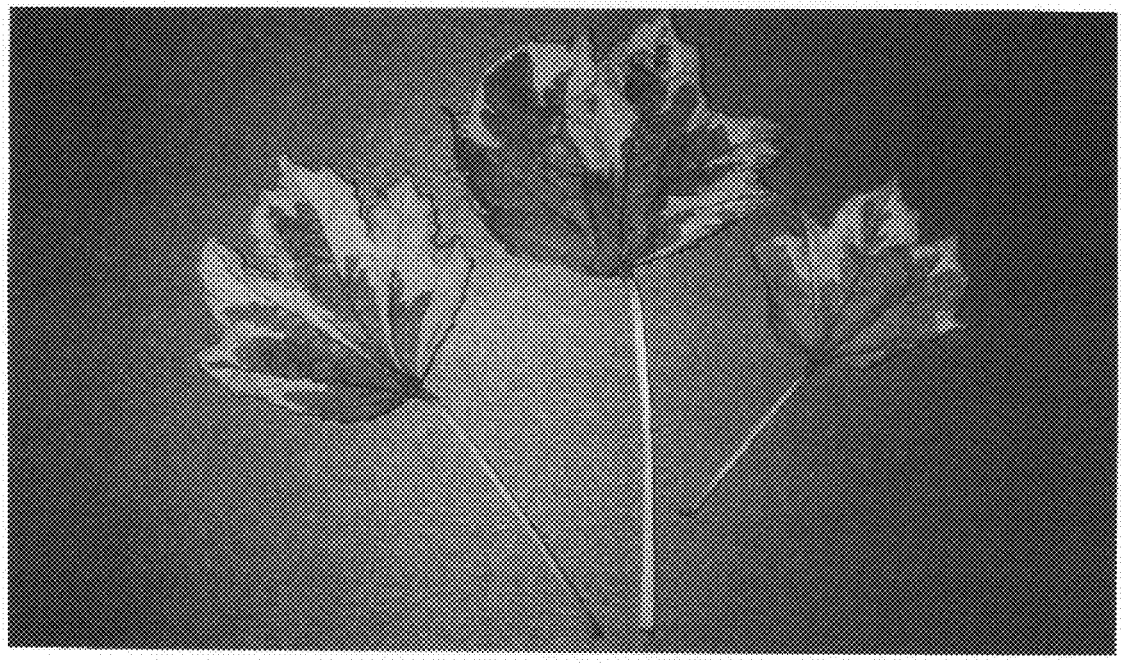
Sheet 2